US006331610B1

(12) United States Patent
Bourinbaiar

(10) Patent No.: US 6,331,610 B1
(45) Date of Patent: Dec. 18, 2001

(54) METHOD FOR TREATING AIDS AND HIV INFECTION USING SELECT PEPTIDES FROM THE BETA SUBUNIT OF HUMAN CHORIONIC GONADOTROPIN

(75) Inventor: Aldar S. Bourinbaiar, New York, NY (US)

(73) Assignee: Metatron, Inc., Deer Park, NY (US)

( * ) Notice: Subject to any disclaimer, the term of this patent is extended or adjusted under 35 U.S.C. 154(b) by 0 days.

(21) Appl. No.: 08/908,371

(22) Filed: Aug. 7, 1997

Related U.S. Application Data

(60) Provisional application No. 60/044,937, filed on Apr. 25, 1997, now abandoned.

(51) Int. Cl.[7] .................................................... A61K 38/00

(52) U.S. Cl. .......................... 530/324; 530/328; 530/329; 530/330; 514/2; 514/15; 514/16; 514/17

(58) Field of Search .................................... 514/12, 15, 2; 530/324, 328, 59, 329, 330

(56) References Cited

U.S. PATENT DOCUMENTS

| | | | | |
|---|---|---|---|---|
| 4,302,386 | | 11/1981 | Stevens | 260/112.5 |
| 4,384,995 | | 5/1983 | Stevens | 260/112.5 |
| 4,526,716 | | 7/1985 | Stevens | 260/112.5 |
| 5,607,974 | * | 3/1997 | Droge | 514/562 |
| 5,677,275 | | 10/1997 | Lunardi-Iskandar et al. | 514/8 |
| 5,700,781 | | 12/1997 | Harris | 514/21 |

OTHER PUBLICATIONS

Bourinbaiar et al. "The Role of Carboxy–Terminal Portion of Beta Subunit of Human Chorionic Gonadotropin in Human Immunodeficiency Virus Infection", *Life Sciences*, 61 (11): pp. PL 149–157, 1997.

Carlsen et al. "Human Chorionic Gonadotropin," *The Journal of Biological Chemistry*, 248 (19):pp. 6810–6827, 1973.

Gallo et al. "Antitumor effects of hCG in KS", *Nature Biotechnology*, 16: pp. 218, Mar. 1998.

Pauwels et al. "Rapid and automated tetrazolium–based colorimetric assay for the detection of anti–HIV compounds", *J Virol Methods*, 20(4): abstract only, Aug. 1988.

Robertson et al. "A Microtiter Cell–Culture Assay for the Determination of Anti–Human Immunodeficiency Virus Neutralizing Antibody Activity", *J Virol Methods*, 20(3): abstract only, Jul. 1988.

Nakashima et al. "Tetrazolium–Based Plaque Assay for HIV–1 and HIV–2, and its Use in the Evaluation of Antiviral Compounds", *J Virol Methods*, 26(3): abstract only, Aug. 1988.

Weislow et al. "New Soluble–Formazan Assay for HIV–1 Cytopathic Effects: Application to High–Flux Screening of Synthetic and Natural Products for AIDS–Antiviral Activity", *J Natl Cancer Inst*, 81(12): abstract only, Apr. 19, 1989.

Gustafson et al. "AIDS–Antiviral Sulfolipids from Cyanobacteria (Blue–Green Algae)", *J Natl Cancer Inst*, 81(16): abstract only, Apr. 16, 1989.

Bergamini et al. "A Tetrazolium–Based Colorimetric Assay for Quantification of HIV–1–Induced Cytopathogenicity in Monocyte–Macrophages Exposed to Macrophage–Colony-Stimulating Factor", *J Virol Methods*, 40(3): abstract only, Dec. 1992.

Shimizu et al. "Lignified Materials as Medicinal Resources. IV. Anti–HIV Activity of Dehydrogenation Polymer of P–Coumaric Acid, a Synthetic Lignin, in a Quasi–in–vivo Assay System as an Intermediary Step to Clinical Trials", *Biol Pharm Bull*, 16(4): abstract only, Apr. 1993.

Hotoda et al. "Biologically Active Oligodeoxyribonucleotides—I: Syntheses and Anti–HIV–1 Activities of 5'–Modified Pentadecadeoxyribonucleotides", *Nucleic Acids Symp Ser*, 29: abstract only, 1993.

Kira et al. "Anti–Tat MTT Assay: a Novel Anti–HIV Drug Screening System Using the Viral Regulatory Network of Replication", *AIDS Res Hum Retroviruses*, 11(11): abstract only, Nov. 1995.

Drossigk et al. "[Effect of Sarcocystis Gigantea Extract (SGE) on the Replication of Human Immunodeficiency Virus]", *Berl Munch Tierarztl Wochenschr*, 109(2): abstract only, Feb. 1996.

Makovsky et al. "Assessment of a Cytoprotection Assay for the Discovery and Evaluation of Anti–Human Immunodeficiency Virus Compounds Utilizing a Genetically–Impaired Virus", *J Virol Methods*, 58(1–2): abstract only, Apr. 1996.

Witvrouw et al. "Inhibition of HIV Type 1 Tat–Mediated Trans–Activation by Oncostatin M in HLtat Cells", *AIDS Res. Hum. Retroviruses*, 11(11): abstract only, Nov. 1998.

Jellinger et al. "A Novel Approach to Assessing the Drug Susceptibility and Replication of Human Immunodeficiency Virus Type 1 Isolates", *J Infect Dis.*, 175(3): abstract only, Mar. 1997.

Kalvatchev et al. "Anti–HIV Activity of Extracts from Calendula Officinalis Flowers", *Biomed Pharmacother*, 51(4): abstract only, 1997.

(List continued on next page.)

*Primary Examiner*—Christopher S. F. Low
*Assistant Examiner*—David Lukton
(74) *Attorney, Agent, or Firm*—Henry D. Coleman; R. Neil Sudol

(57) ABSTRACT

The present invention relates to select peptides of the carboxy terminal and aminoterminal portion of the beta unit of hCG and pharmaceutically acceptable derivatives thereof that can be used for controlling retroviral, e.g., human immunodeficiency virus (BV infections. The invention comprises a method in vitro as well as in vivo for prevention and/or treatment of acquired immune deficiency syndrome (AIDS) at pharmacological doses of beta hCG-derived peptides and pharmaceutically acceptable derivatives thereof which are sufficient to exert an anti-HIV effect for a sufficient period of time.

18 Claims, 3 Drawing Sheets

OTHER PUBLICATIONS

Longhi et al. "Enzyme Immunoassay for Human Chorionic Gonadotropin Using Monoclonal Antibodies Elicited witha Synthetic Peptide", *J Immunol Methods*, 92(1): abstract only, Aug. 1986.

Kochanowska et al. "Human Serum Immunoglobulins Binding to Synthetic Fragments of Human Chorionic Gonadotropin", *Arch Immunol Ther Exp*, 43(3–4): abstract only, 1995.

S. Birken. "Chemistry of Human Choriogonadotropin", *Ann Endocrinol*, 45(4–5): abstract only, 1984.

Wehmann et al. "Metabolic and Renal Clearance Rates of Purified Human Chorionic Gonadotropin", *J Clin Invest*, 68(1): abstract only, Jul. 1981.

Jones et al. "Phase I Clinical Trail of a World Health Organisation Birth Control Vaccine", *Lancet*, 1(8598): abstract only, Jun. 1988.

Ohio State University. "Progress in the Development of Human Chorionic Gonadotropin Antifertility Vaccines", *Am J Reprod Immunol*, 35(3): abstract only, Mar. 1996.

Kaneda et al. "Synthetic Cell–Adhesive Laminin Peptide YIGSR Conjugated with Polyethylene Glycol has Improved Antimetastatic Activity Due to a Longer Half–Life in Blood", *Invasion Metstasis*, 15(3–4): abstract only, 1995.

Wehmann et al. "Characterization of a Carboxyterminal Peptide Fragment of the Human Choriogonadotropin Beta-Subunit Excreted in the Urine of a Woman with Choriocarcinoma", *J Clin Invest*, 71(2): abstract only, Feb. 1983.

Bourinbaiar et al. "Effect of Human Chorionic Gonadotropin (hCG) on Reverse Transcriptase Activity in HIV–1 Infected Lymphocytes and Monocytes", *FEMS Microbiology Letters*, 96: pp. 27–30, 1992.

Bourinbaiar et al. "Anti–HIV Effect of Beta Subunit of Human Chorionic Gonadotropin", *Immunology Letters*, 44: pp. 13–18, 1995.

Bourinbaiar et al. "Inhibitory Effect of Human Chorionic Gonadotropin (hCG) on HIV–1 Transmission from Lymphocytes to Trophoblasts", *FEBS*, 309(1): pp. 82–84, Aug. 1992.

Carlsen, Robert B., et al., "Human Chorionic Gonadotropin", *J. Bio. Chem.*, 248(19):6810–6827 (1973).

Bourinbaiar, Aldar S., et al., "The Role of Carboxy–Terminal Portion of Beta Subunit of Human Chiorionic Gonadotropin in Human Immunodeficiency Virus Infection", *Pharm. Letters*, 61(11):149–157 (1997).

Gallo, Robert C., et al., "Antitumor effects of hCG in KS" (correspondence), *Nature Biotechnology*, 16:218 (1998).

* cited by examiner

METHOD FOR TREATING AIDS AND HIV INFECTION USING SELECT PEPTIDES FROM THE BETA SUBUNIT OF HUMAN CHORIONIC GONADOTROPIN

This application claims priority from provisonal application serial no. 60/044,937, filed Apr. 25, 1997, now abandoned.

THE FIELD OF INVENTION

The present invention is directed to the method of preventing and treating AIDS and HIV infection using select peptides derived from the beta subunit of human chorionic gonadotropin (hCG), peptide fragments thereof and pharmaceutically acceptable peptide derivatives thereof having antiretroviral activity.

BACKGROUND OF THE INVENTION

Human immunodeficiency viruses (HIV) of type 1 and 2 are lentiviruses from the family of retroviruses that are believed to cause acquired immunodeficiency syndrome (AIDS). Human T lymphotropic viruses (HTLV) of type 1 and 2 are also human retroviruses and cause adult T cell leukemia, neurodegenerative diseases, and immunodeficiency. Thus, there are several types a of pathogenic human retroviruses and as used herein HIV refers to them generically. The transmission of HIV through sexual contact and during pregnancy accounts for up to 90% of AIDS cases worldwide. This transmission is initiated by the passage of HIV across the mucosal barrier of sexual organs or placenta when exposed to infectious body fluids such as semen, vaginal secretions. or blood. The remaining AIDS cases are due to the transfusion of HIV-contaminated blood, needle sharing among intravenous drug users, accidental exposure to HIV-contaminated body fluids during invasive procedures, and other situations wherein infectious virus can come into direct contact with susceptible human tissues.

Effective compounds with anti-HIV activity that could be used to prevent and/or treat AIDS are still lacking. Although initially the results with certain anti-HIV agents, e.g., azidothymidine (AZT) appeared to be promising, it has become clear that toxicity or undesirable side effects of such agents are incompatible with their antiviral activity when used at an effective pharmaceutical concentration (Bourinbaiar & Fruhstorfer, *Cell Pharmacol AIDS Sci*, 3:163–9, 1996). Similar concerns regarding toxicity have arisen upon use of recently introduced new drugs, such as HIV protease inhibitors. Thus, present methods of preventing and treating AIDS and HIV infection are limited and it is thus obvious that better alternative compounds devoid of toxicity and of undesirable side effects must be sought.

The present inventor has contributed to the discovery of several classes of pharmaceutical compounds which may be useful in inhibiting the replication of HIV and other viral pathogens (Bourinbaiar & Lee-Huang, *Adv. Exp. Med. Biol.* 374:71–89, 1995). Among them are:

- Pregnancy steroid hormones, progesterone and estrogen, which were found to inhibit HIV replication in macrophages at doses smaller than can be attained by taking ordinary birth control pills.
- Sulphated polysaccharide, dextran sulphate, has been described as an agent suppressing cell-to-cell HIV transmission, associating for the first time the mechanism of this compound with the prevention of cell-mediated viral spread.
- The low doses of interferon taken orally as means to treat and prevent AIDS and HIV spread in mucosal environment.
- A family of heterocyclic compounds named coumarins as potent anti-HIV drugs acting as protease inhibitors. Various derivatives of coumarins are used mostly as oral anticoagulants, e.g., coumadin or warfarin.
- A high molecular weight factor of protein origin has been discovered in cells of placental origin as a possible candidate molecule that may help to support the fertility and prevent HIV infection during pregnancy.
- An oral immune modulator of bacterial origin, bestatin, as an agent with anti-HIV activity. Three clinical studies have shown that this molecule is safe and beneficial to AIDS patients.
- An antibiotic, gramicidin, was found to display anti-HIV, anti-herpes, and sperm-immobilizing properties which makes this compound an attractive candidate for a topical contraceptive with prophylactic capacity against sexually transmitted diseases of viral and microbial origin.
- N-tosyl-L-lysyl-cbloromethylketone (TLCK)—a serine protease inhibitor and HIV antagonist.
- The immunomodulating agent, levamisole, previously used as a deworming agent and as a drug for adjuvant therapy of malignant carcinomas. has been reported as an anti-HIV agent.
- Two proteins derived from medicinal plants were discovered to have anti-herpes activity.
- Several steroid and non-steroidal anti-inflammatory drugs such as dexamethasone, prednisone, acetylsalicylic acid (aspirin), ibuprofen, indoprofen, naproxen, nordihydroguaiaretic acid, indomethacin, etc., were tested for their activity against HIV. Some of these compounds such as prednisone have been found to be effective in delaying the progression to AIDS.
- Another protease inhibitor, 4'-acetarmdophenyl 4-guanidinobenzoate, an experimental vaginal contraceptive was identified as an anti-HIV agent with activity corresponding to the levels attainable locally.
- Cyclosporin—an immunosuppressor used in transplant patients—was described as having anti-HIV activity.
- A new class of antiviral agents selected from histamine type 2 receptor antagonists such as famotidine, ranitidine, cimetidine have been identified, with activity at doses that can be attained by oral administration of a standard clinical dose. Independent clinical trials in HIV+ patients have shown beneficial effect without any adverse side-effects.

It is thus clear that the potential number of compounds that can be used in preventing and treating AIDS is quite large. However, among the many drugs that can be used today as anti-HIV agents the most promising ones are those which are naturally occurring in the human body and as a consequence are less toxic and more effective.

Human chorionic gonadotropin (hCG) is mainly known as a glycoprotein hormone secreted by the placenta and is essential for the maintenance of pregnancy. The alpha chain of hCG heterodimer is identical to alpha subunits of related glycoprotein hormones from the pituitary such as lutropin (LH), follitropin (FSH), and thyrotropin (TSH). Each hormone has a distinct beta subunit which confers receptor-binding specificities. The first 114 amino acids of beta chains of hCG and LH exhibit 86% homology as they differ by only 16 residues. However, the CTP of hCG is unique to this hormone since the beta subunit of LH lacks COOH-terminal extension. Both hormones exert their effect through a shared hCG/LH receptor—G-protein coupled single polypeptide that spans the plasma membrane seven times. As hCG-CTP does not bind to the receptor, it is believed that this portion has no biological or immunogenic activity. Due to the unique nature of the COOH-terminus of beta hCG, synthetic fragments comprising residues 109–145 have been investigated for the last 15 years as a birth control vaccine. A phase II trial of a such vaccine has recently been reported demonstrating the feasibility of this approach.

For reasons that are little understood, tumors of various origins appear to express hCG and hence, this hormone serves as an important diagnostic marker of malignancy. hCG was first proposed as an anti-tumor protein when it was observed that 7,12-dimethylbenz[a]anthracene-inducible breast carcinoma was abolished in pregnant rats or rats treated with hCG. In line with this finding, Lunardi-Iskandar et al., have recently suggested that high doses of hCG and beta hCG may be useful for the treatment of Kaposi's sarcoma by causing apoptosis in neoplastic cells. Clinical trials carried out following this report seem to lend support to this proposal.

It is now increasingly clear that hCG is not unique to pregnancy and may be responsible for a number of unrelated physiological functions. Many microorganisms and some relict invertebrates, such as horseshoe crabs, produce beta hCG-like molecules suggesting that they may play a critical role required for their survival throughout evolution. For example, Saccharomyces cerevisiae yeast appear to secrete a substantial amount of hCG-like substance which translates to the curious fact that all tested commercial beers have been found to contain this hormone. hCG is also produced in non-pregnant humans by a wide range of non-malignant cells including pituitary and T lymphocytes. hCG was found to be secreted during mixed lymphocyte reaction which results from cell-cell contact of lymphocytes. This may indicate that specialized human T lymphocytes such as cytotoxic T lymphocytes (CTL) may be responsible for the control of HIV replication by producing hCG when in contact with HIV-infected cells. Thus, hCG may be the host factor responsible for delaying the progression to AIDS and AIDS associated clinical symptoms such as cancer, opportunistic infections, wasting, and endocrine abnormalities.

The hCG/LH receptor, originally thought to be found exclusively on gonadal cells, has been now found on various cells outside of the reproductive compartment. A functional 50 kD receptor with affinity to hCG has recently been discovered on human T lymphocytes as well. The presence of this receptor on the immunocompetent cells may explain the fact that picomolar quantities of hCG can exert a strong chemotactic stimulus for T lymphocytes, monocytes, and neutrophils. Incidentally, several reports indicate that chemoattractant chemokines such as RANTES and macrophage inflammatory protein 1 (MIP-1alpha and beta) act as HIV antagonists through competition with shared cellular ligands which belong to G-linked receptors of the same family as hCG/LH receptor.

The present inventor was first to discover that pregnancy-associated glycoprotein hormone human chorionic gonadotropin (hCG) and its beta subunit can display anti-HIV activity at non-toxic doses. Dimer hCG as well as the beta hCG subunit can suppress HIV replication within the physiological dose range, suggesting that this hormone is responsible for the low rate of HIV transmission in utero. At least in an in vitro model hCG has been found to prevent cell-to-cell HIV transmission resulting from physical contact of virus-infected lymphocytes with trophoblasts—the fetal cells lining the outer layer of the placenta. Furthermore, low dose hCG injections appeared to have beneficial effect in AIDS patients by reducing the viral burden and reversing HIV infection-associated endocrine abnormalities. In a model of transgenic mice carrying defective HIV provirus, hCG was found to protect newborn mice from death and reduce HIV infection-associated skin lesions and wasting. In this model, both hCG and beta hCG have been shown to decrease HIV mRNA and HIV protein expressions. In view of such findings it is clear that hCG, which shares the same characteristics with chemoattractant chemokines, is an ubiquitous multifunctional molecule with potential in AIDS prevention and therapy. However, the active site(s) on the hCG molecule responsible for the anti-HIV effect were not identified as it was not clear to those skilled in the art whether hCG itself or contaminating molecule unrelated to hCG, found in commercial hCG preparations, was responsible for the anti-HIV effect.

Amino acids are the main components of peptides and proteins but can also be found in a free form. Amino acids are the most important class of organic substances in the cell and human body fluids. The beta hCG is a subunit specific to the most important pregnancy hormone—hCG. The N-terminal, core and C-terminal portions (CTP) of beta hCG are defined as each being approximately 50 amino acid residues long. The entire beta subunit of hCG is a 145 amino acid long peptide and may be represented by the general formula $S_1KEPLRPRCR_{10}PINATLAVEK_{20}EGCPVCITVN_{30}TTIC$-
AGYC
$PT_{40}MTRVLQGVLP_{50}ALPQVVCNYR60DVRFESIRL$-
$P_{70}GCPRGV$
$NPVV_{80}SYAVALSCQC_{90}ALCRRSTTDC_{100}GGPKDHPL$-
$TC_{110}DDP$
$RFQDSSS_{120}SKAPPPSLPS_{130}PSRLPGPSDT_{140}PILPQ_{145}$:
Sequence I.D. No. 1.

Wherein each individual letter corresponds to a specific amino acid according to the established one-letter code nomenclature as follows: A=Alanine; R=Arginine; N=Asparagine; D=Aspartic acid; C=Cysteine; E=Glutamic acid; Q=Glutamine; G=Glycine; H=Histidine; I=Isoleucine; L=Leucine; K=Lysine; M=Methionine; F=Phenylalanine; P=Proline; S=Serine; T=Threonine; W=Tryptophan; Y=Tyrosine; V=Valine.

The beta and alpha subunits of hCG are glycoproteins, meaning that in addition to amino acids they contain various sugar molecules or oligosaccharides. Prior art indicates that gonadotropin hormones including hCG are not active if they are not glycosylated. The degree of activity of glycoprotein hormones is reduced when the glycosylation is altered.

The present invention relates to compounds selected from a group of peptides representing beta hCG comprising CTP, N-terminal end of beta hCG, or peptide fragments thereof containing at least 4 amino acid units for use as a new class of pharmaceutical agents with anti-HIV activity. The activity of these peptides can be observed even when they are not glycosylated.

OBJECTS OF THE INVENTION

It is an object of the present invention is to provide a method for suppressing HIV replication.

It is also an object of this invention to provide a method to treat and prevent the symptoms of AIDS that may occur as a consequence of HIV replication in vivo.

It is also an object of this invention to provide a method to prevent the transmission of HIV in vitro.

It is an additional object of this invention to provide a method to prevent the transmission of HIV in vivo during pregnancy or during sexual contact.

It is a further object of this invention to provide a method to prevent or treat HIV infection using the carboxy-terminal portion of beta hCG, the N-terminal portion of beta hCG, anti-HIV effective peptide fragments thereof, or peptide mimicking derivatives thereof, either alone or in combination with drugs having anti-HIV activity.

These and other objects of the invention will be apparent from the specification which follows hereafter.

SUMMARY OF THE INVENTION

In search of the active element within hCG, more specifically within its beta subunit, it has been discovered unexpectedly by the present inventor that the carboxyterminal portion (CTP) of hCG plays the major role in inhibiting HIV replication. The $NH_2$-terminal portion also had an effect, but the hCG core region had practically no effect. This discovery was totally unexpected in as much as the C-terminal and N-terminal portions were believed to be biologically inactive. This discovery was unexpected even to those skilled in the art as only the core region of beta hCG was postulated to have some activity due to its sequence similarity with certain growth hormones such as PDGF and related hormones of the same family. Furthermore, such peptides displayed biological activity despite the fact that they were nonglycosylated. Peptides representing carboxy-terminal portion(s) of beta hCG are known in the art and the U.S. Pat. No. 4,691,006, which is incorporated by reference, discloses some of them.

The present invention, therefore, comprises a method for preventing or inhibiting HIV replication and spread in vitro as well as in vivo using select peptides (peptide fragments) of beta hCG. Such peptides are derived either from the carboxy terminal (hCG-CTP) or amino terminal end of beta hCG, alone or in combination with drugs having anti-HIV activity. The present invention relates to the discovery that a peptide fragment corresponding to amino acids 100–145 of beta hCG and peptide fragments thereof containing at least four amino acid units exhibit unexpected anti-HIV activity. The present invention also relates to the discovery that a peptide fragment corresponding to amino acids 1–50 of beta hCG and peptide fragments containing at least four amino acid units exhibit unexpected anti-HIV activity. Such activities were observed even though the peptides were not glycosylated. Thus, the present invention is directed to the use either of a peptide fragment of at least four amino acids derived from the N-terminal end of beta hCG (witch corresponds to amino acids 1–50) or a peptide fragment of at least four amino acids derived from hCG-CTP (which corresponds to amino acids 100–145 of beta hCG). More preferably, the peptide fragments which are used in the present invention correspond to amino acids 1 to 45 or 106 to 145 of beta hCG or a peptide fragment thereof containing at least four amino acids. In a preferred aspect of the present invention, a five amino acid peptide fragment of the N-terminal end or hCGT-CTP is used to inhibit HIV replication In a more preferred aspect of the present invention, the peptide fragment is at least about 10 amino acid units in size, even more preferably about 20 amino acid units in size and in an even more preferred aspect, the fragment is at least about 40 amino acids units in size. One or more of these peptides is administered in an anti-HIV effective amount to patients who have been infected with HIV in order to inhibit the growth, replication and/or elaboration of HIV and to delay the onset or prevent the occurrence of AIDS in HIV positive patients.

More specifically, the invention comprises a method for suppressing HIV replication and spread by employing therapeutically effective doses of the N-terminal end of hCG or hCG-CTP or peptide fragments thereof containing at least four amino acid units, thereof as active ingredients in pharmaceutical formulations administered by accepted means of drug delivery known in the art, e.g., oral parenteral including intramuscular and intravenous, buccal, transdermal and related routes. of administration. The preferred method of delivery is intravenous or intramuscular delivery in an amount and for a period of time both of which are sufficient to exert an inhibitory effect on HIV replication and spread of HIV with the goal of treating or preventing AIDS.

The invention also comprises a method for preventing the mother-to-fetus (vertica) and sex-borne (horizontal) spread of HIV by employing therapeutically effective doses of N-terminal end peptides or hCG-CTP peptides and derivatives thereof as described hereinabove as active ingredients in pharmaceutical formulations in an amount and for a period of time both of which are sufficient to exert a protective effect against vertical and horizontal transmission of HIV.

DETAILED DESCRIPTION OF THE INVENTION

Figure 1:
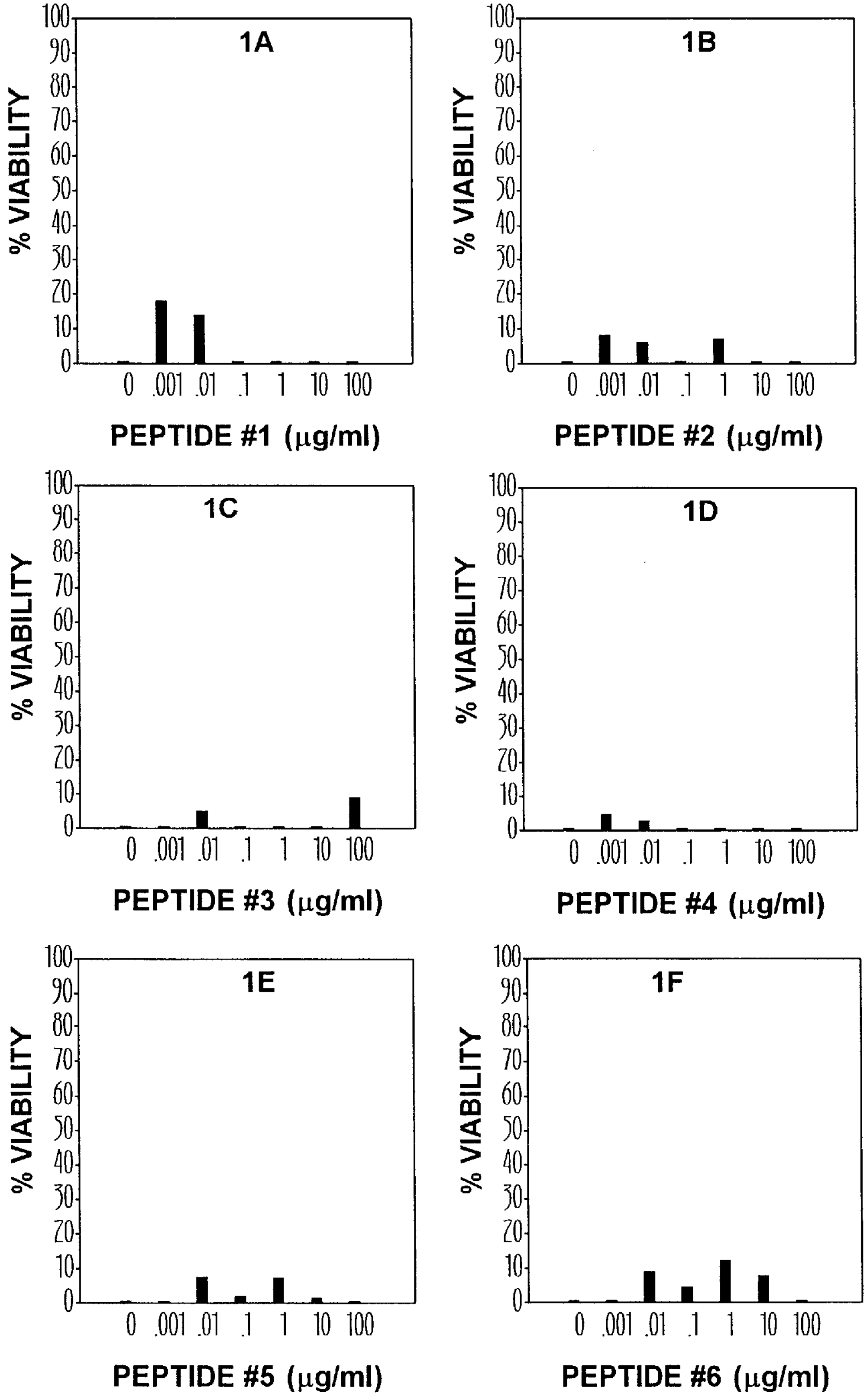
FIG. 1 shows the anti-HIV effect of peptides representing N-terminal and core regions of beta hCG.

Effective anti-AIDS compounds that can display anti-HIV activity without concombinant toxicity are still needed. This invention provides a method for treating and preventing HIV spread and replication by using peptide fragments of hCG as agents with anti-HIV activity.

The term "peptide fragment(s)" is used throughout the specification to describe compounds comprising at least four amino acids in size which are derived from peptide fragments corresponding to amino acids 1–50 or 100–145 of beta hCG, peptide fragments. The term "peptide fragments" includes peptides in one or more of their pharmaceutically acceptable form(s) including pharmaceutically acceptable salt forms.

The present inventor has spent considerable time researching compounds which might be useful in preventing the transmission of HIV and for the treatment of HIV infections. As a resulting several potentially useful antiviral compounds were identified. However, it is clear that the efforts in preventing the spread of HIV and treating AIDS will depend on the larger choice of diverse types of pharmaceutical agents with antiviral potential that could be used either alone or in combination.

The present method represents such an approach.

The therapeutic aspect according to the present invention relates to methods for treating HIV infections in humans comprising administering anti-viral effective amounts of the peptide fragments according to the present invention to a patient to inhibit the growth or replication of the virus in that patient being treated. Other method aspects of the present invention relate to in vitro and in vivo methods for inhibiting the growth, replication or elaboration of HIV. Other method aspects of the present invention relate to prophylactic methods for preventing an HIV infection in a human, including methods which are directed to the preventing of infection which may occur from an infected mother to her fetus during pregnancy. Methods directed to the treatment of AIDS comprising administering to a patient who exhibits AIDS symptoms an AIDS-treating effective amount of a peptide fragment according to the present invention is another aspect.

Pharmaceutical compositions based upon the beta hCG peptide fragments comprise the above-described peptide fragments in a therapeutically effective amount for treating HIV, optionally in combination with a pharmaceutically acceptable additive, carrier or excipient. One of ordinary skill in the art will recognize that a therapeutically effective amount will vary with the infection or condition to be treated, its severity, the treatment regimen to be employed, the pharmacokinetics of the agent used, as well as the patient treated.

In the pharmaceutical aspect according to the present invention, the compound according to the present invention is formulated preferably in admixture with a pharmaceutically acceptable carrier. In general, it is preferable to administer the pharmaceutical composition in orally-administrable form for example, utilizing liposomes, but certain formulations may be administered via a parenteral, intravenous, intramuscular, transdermal, buccal, subcutaneous, suppository or other route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, pharmaceutically acceptable salt and pro-drug forms of the compounds, especially including various salt forms of the peptide fragments may be preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within therapeutically active formulations according to the present invention is an effective amount for treating or preventing the HIV infection or condition (AIDS). The appropriate dosages for an individual subject will depend on the levels of hCG peptide derivatives attained in blood, serum plasma, and other human body fluids such as semen, vaginal excretions, and amniotic fluid, which can be readily determined by one of ordinary skill in the art.

The dosage used in the present invention is that which is a therapeutically effective amount for inhibiting the replication, elaboration and/or the growth of HIV in the patient. The present method also functions to delay and/or prevent the onset of AIDS in HIV positive patients. The levels used are preferably not higher than about 100–150 mcg/ml (plasma concentration or other body fluid) for systemic use, and topical doses not higher than 100–500 mg/ml (in the topical formulation) are preferable. In the present invention, an effective amount of peptide is that amount which produces a blood concentration level of peptide ranging from about 1 nanogram/ml (ng/ml) to no higher than about 100–150 micrograms per ml (mcg/ml). In general, in order to produce a blood concentration level of peptide of about 1 ng/ml to about 100 mcg/ml, peptide is administered in at least a weekly dose range of about 1 mg to about 2.5 g, preferably at least 10 mg. If an oral mode of delivery is used then the administration of daily doses is preferred and these doses preferably range from about 200 micrograms to about 1 g to attain systemic levels between 1 ng and 150 mcg per ml of plasma or blood.

The doses for systemic use can be given once a day or divided doses may be administered daily for a period of time as indicated by the exigencies of the therapeutic situation. The doses for topical use can be administered preferably before sexual intercourse as means to inhit HIV spread in the mucosa. The maximum daily dose for either use should preferably not be higher than 500 mg. The use of higher doses may be limited by the physical capacity of the human body to accommodate said doses or by overdose-associated toxicity. The preferred dosage must be within acceptable non-toxic range given for a period of time deemed necessary. hCG peptides as agents possessing anti-HIV activity can be used alone or given in combination with other compounds selected from a group specified in the body of invention including but not limited to warfarin (oral HIV protease inhibitor), coumarins, interferon, bestatin, levamisole, estrogen, progesterone, dexamethasone, indomethacin, cimetidine, acetaminophen, and gramicidin, among numerous others. The lowest possible effective dosage can be calculated so as to attain sufficient levels to achieve optimal activity in combination or alone. The concentration ranges set forth herein are exemplary only and are not intended to limit the scope or practice of invention. The adjustment and optimization of dosage is well within the skill of the practitioner in the art and it is apparent that certain changes and modifications may be practiced within the scope of the appended claims without requiring the practitioner to engage in undue experimentation.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration.

To prepare the pharmaceutical compositions according to the present invention, a. therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

The compounds according to the present invention also may advantageously be employed prophylactically to prevent infection or to prevent the occurrence of clinical symptoms associated with the viral infection Thus, the present invention also encompasses methods for the prophylactic treatment of HIV, especially to prevent or limit infection from a pregnant mother to a fetus the mother is carrying, or during sexual intercourse. This prophylactic method comprises administering to a patient in need of such treatment an amount of a compound according to the present invention effective for alleviating, and/or preventing the viral infection. It is particularly preferred in this aspect of the present invention that the compound which is used should be maximally effective against the virus and should exhibit a minimum of toxicity to the patient (favorable therapeutic index).

The inventor has demonstrated experimentally that in an antiviral assay based on evaluation of HIV-caused cell death, the CTP of hCG can protect HIV-exposed T lymphocytes from cell death at inhibitory concentration ($IC_{50}$) equal to 100 nanograms per ml (ng/ml). It has been determined that this concentration and concentrations up to 1,000-fold higher are not toxic to cells employed in this assay. This discovery was totally unexpected since there is no evidence in the prior art that CTP of beta hCG has any biological activity per se. Furthermore, the activity was observed with CTP peptides devoid of sugar moieties. This was also unexpected since glycoproteins are not generally active when they are deglycosylated.

A similar, albeit less potent effect was observed with N-terminal peptides of hCG which was most active at the lowest tested 1 ng/ml concentration. It is thus apparent, to those skilled in the art, that the administration of suitable doses of peptide fragments of hCG can achieve desirable anti-HIV effect in vivo without being toxic to the human host. Furthermore, it appears that as in vitro activity of hCG can be reproduced in vivo, peptides derived from beta hCG would be also effective in vivo and are thus of potential therapeutic significance.

The present inventor has discovered that select peptide derivatives of hCG can display anti-HIV activity in vitro at nanogram to microgram range concentrations and has proposed that these compound might be useful in preventing and treating HIV replication. The effective doses were non-toxic, thus indicating that the antiviral effect was specific.

Thus it can be readily seen that select peptides of beta hCG are responsible for the suppression of HIV replication and its spread. It can be also seen that antivirally effective doses of said compounds are not correlated with toxicity and that doses defined in vitro will be adequate to prevent and treat HIV in vivo.

The present invention is now described, purely by way of illustration, in the following examples. It will be understood by one of ordinary skill in the art that these examples are in no way limiting and that variations of detail can be made without departing from the spirit and scope of the present invention.

EXAMPLE 1

Preparation of Synthetic hCG Peptides.

Overlapping peptides of hCG subunit were synthesized using the solid phase method. Boc (MeBzl) resins were used throughout and completeness of amino group consumption checked aver each amino acid addition. Peptides were cleaved from the resin using hydrofluoric acid and were purified by a series of chromatographic steps employing reverse phase HPLC C-18 columns. Products were eluted with linear gradients of 0.1% trifluoroacetic acid, 0.05 M ammonium acetate or 0.05 M phosphate buffers containing 60% acetonitrile. The purity of peptides was checked at various stages of purification and on the final products using thin layer chromatography on silica gel and cellulose, paper electrophoresis and HPLC reverse phase chromatography. Amino acid analysis was performed on all final products. The amino acid sequence and the method of preparation of peptides #1–#10 can be found in Stevens et al. (*Immunol Lett*. 12:11–18, 1986). Peptide 111–145$P_6$-C containing a spacer group consisting of six additional proline residues followed by cysteine and attached to the C-tenninus end of beta hCG fragment was prepared as described in Stevens et al. (*Am J Reprod Med* 1:307–314, 1981). Peptide 111–148 was synthesized according to the amino acid sequence described by Carlsen et al. (*J Biol Chem* 248:6810–6827, 1973). The peptides used in this Example and in Example 2 are shown in Table 1.

TABLE 1

Size and position of tested peptide fragments relative to amino acid sequence of hCG.

| hCG peptides | Spanning regions | Peptide Sequence | |
|---|---|---|---|
| #1 | 20–32 | $K_{20}$EGCPVCITVN$_{30}$TT | Sequence ID No. 2 |
| #2 | 30–42 | $N_{30}$TTICAGYCPT$_{40}$MT | Sequence ID No. 3 |
| #3 | 50–62 | $P_{50}$ALPQVVCNYR$_{60}$DV | Sequence ID No. 4 |
| #4 | 60–72 | $R_{60}$DVRFESIRLP$_{70}$GC | Sequence ID No. 5 |
| #5 | 80–92 | $V_{80}$SYAVALSCQC$_{90}$AL | Sequence ID No. 6 |
| #6 | 90–102 | $C_{90}$ALCRRSTTDC$_{100}$GG | Sequence ID No. 7 |
| #7 | 100–112 | $C_{100}$GGPKDHPLTC$_{110}$DD | Sequence ID No. 8 |
| #8 | 120–132 | $S_{120}$SKAPPPSLPS$_{130}$PS | Sequence ID No. 9 |

TABLE 1-continued

Size and position of tested peptide fragments relative to amino acid sequence of hCG.

| hCG peptides | Spanning regions | Peptide Sequence | |
|---|---|---|---|
| #9 | 106–145 | HPLTC$_{110}$DDPRFQDSSS$_{120}$SKAPPPSLPS$_{130}$ PSRLPGPSDT$_{140}$PILPQ$_{145}$ | Sequence ID No. 10 |
| #10 | 130–145 | S$_{130}$PSRLPGPSDT$_{140}$PILPQ$_{145}$ | Sequence ID No. 11 |
| #11 | 111–145P | DDPRFQDSSS$_{120}$SKAPPPSLPS$_{130}$ PSRLPGPSDT$_{140}$PILPQ$_{145}$PPPPPPC | Sequence ID No. 12 |
| #12 | 111–148[b] | See Carlsen, et al., J. Biol. Chem., 248, 6810–6827, 1973. | |

[a]This fragment contains a spacer consisting of 6 proline and 1 cysteine residue at the C-terminal end.
[b]The amino acid sequence of this peptide was originally described as the C-terminal peptide of beta hCG but was later found to be incorrect.

Determination of Anti-HIV Effect.

MT-4 T lymphocytes (5×10$^4$ cells/ml) were seeded in 96well plates and exposed to IIIB strain of HIV-1 (at MOI equal to 100 infectious doses) in the presence of ten-fold, serial dilutions of hCG peptides (range 100 mcg–1 ng per ml). The term mcg stands for microgram, i.e., parts per million, and ng stands for nanogram i.e., parts per billion. The tests were repeated three times with duplicates for each dilution of an individual peptide. All cultures were grown in RPMI-1640/10% FBS medium supplemented witi L-glutamine and penicillin/streptomycin. The culture plates were kept in a humidified incubator with 5% $CO_2$ at 37° C. After 5 to 7 days of incubation most of the HIV-infected MT-4 were killed, while most of the mock-infected cells remained alive. Although lymphocytes in some wells containing certain hCG peptides appeared to be dead, the cells in other wells were less affected. This difference in the survival pattern, indicative of the antiviral activity, was quantitated by tetrazolium salt XTT assay. This assay is based on the rationale that the viability of MT-4 correlates directly with the activity of mitochondrial hydrogenases converting XTT into optically dense formazan dye. This method is commonly used for the mass-screening of anti-HIV drugs and obtained results are equivalent to the RT assay or p24 antigen ELISA based on measuring the viral release and replication. At the appropriate time 1 mg/ml of XTT (Sigma, St Louis, Mo.) was nixed with 1% w/v phenazine methosulfate (Aldrich, Milwaukee, Wis.) and 20 mcl of the mixture was added to the wells for 4 hours. The optical density of formazan was then determined in a plate reader at 450 nm with reference filter at 620 nm. The proportion of surviving MT-4 cells treated with hCG peptides was calculated as a function of the viability of mock-infected cells in relation to positive control wells containing untreated cells dead from exposure to HIV. The following equation was used to estimate the protective effect hCG peptides against HIV-caused cell killing:

$$\text{Viability}=100\%\times[(OD_T)-(OD_D)]/[(OD_M)-(OD_D)]$$

Where $OD_T$ is optical density values of culture wells treated with test peptides; $OD_M$ optical density of mock-infected cells; $OD_D$ light absorbance values of untreated cells dead from exposure to HIV.

EXAMPLE 2

The serial ten-fold dilutions (100 mcg–1 ng per ml) of 6 different synthetic peptides representing N-terminal and core region of hCG were tested for their effect on HIV replication (FIG. 1). Judging from the observation under the microscope, the presence of some beta hCG peptides seemed to protect MT-4 T lymphocytes from HIV-caused cytopathic effect, i.e., syncytia formation and cell death. The viability of cells appeared to be dependent on the concentration of the peptide and was, accordingly, measured by XTT assay. The experimental OD values obtained from three independent experiments were converted to percentile scores and means corresponding to each serial dilution of the peptide are shown as bars on a 100% scale. In these experiments the viability of MT4 was determined after 5–7 days of continuous presence of the virus and hCG peptide fragment in the target cell culture.

The anti-HIV effect of the first 6 peptides that span the N-terminal and core portion of hCG molecule are shown in FIG. 1. Although the peptide #1 (20–32), from N-terminal region of beta hCG, was found to be active at nanogram doses, the peptides corresponding to the core fragment of hCG had not shown any significant activity.

EXAMPLE 3

The synthesis of peptides used in this example and determination of anti-HIV effect were carried out as described in Example 1. The panel consisting of six graphs in FIG. 2 displays the effect of synthetic peptides that encompass predominantly the COOH-terminal portion of beta hCG. The anti-HIV effect was observed with peptides starting from the position 100 and ending at the position 145 which represents the COOH-terminal portion of beta hCG. Short peptides containing 10–15 amino acids (e.g., #7, #8, #10) within this region were active but the most striking effect was observed with the peptide #9 (106–145) containing 40 amino acid residues of the CTP. The dose response curve for this peptide is bell-shaped and resembles the effect of the beta subunit reported earlier. The most potent concentration of this peptide is equal to 100 ng/ml—the dose at which 63% of MT-4 cells were able to survive after 6 days of exposure to HIV.

EXAMPLE 4

Figure 2:
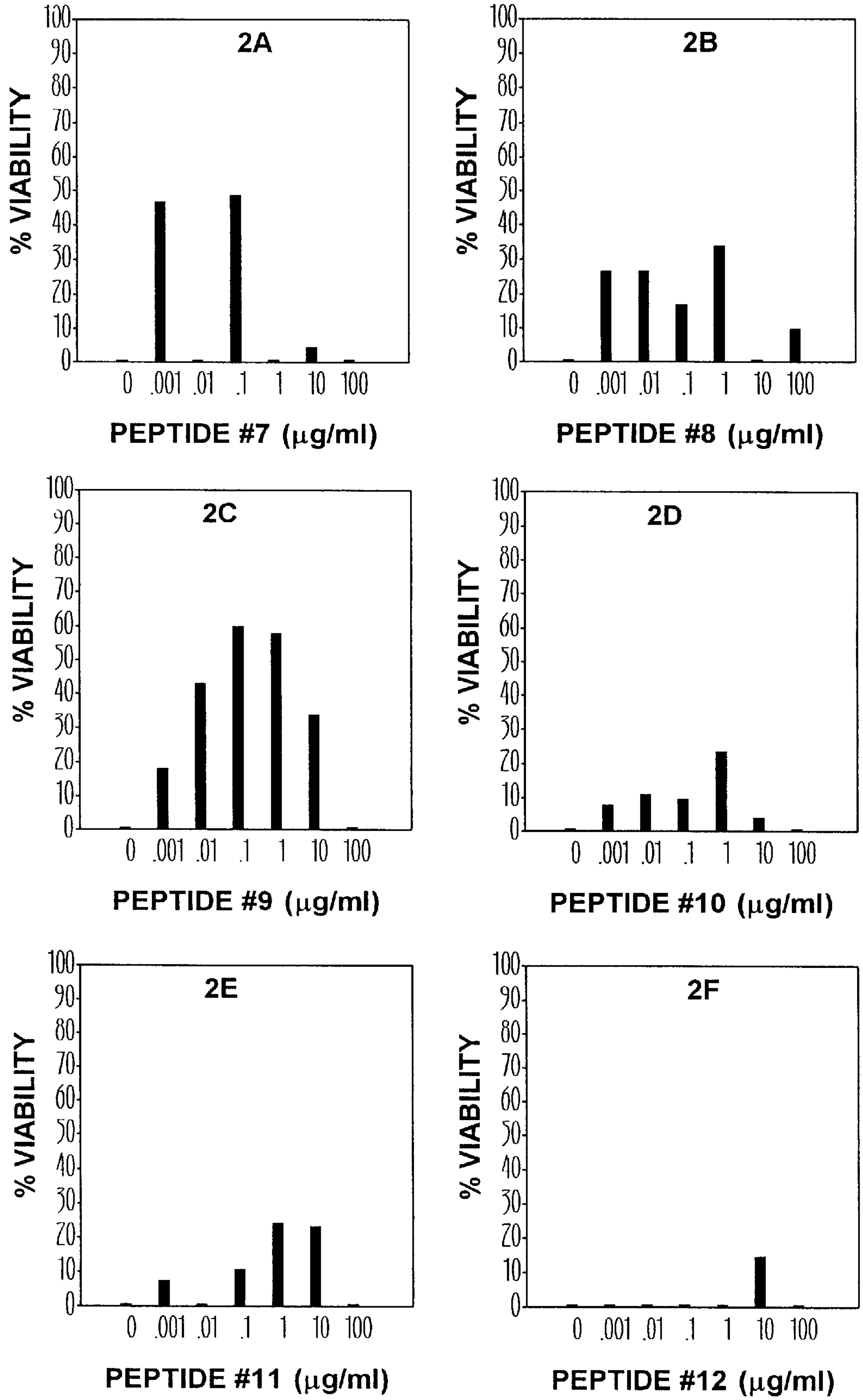
FIG. 2 shows the anti-HIV effect of peptides representing C-terminal portion of beta hCG.

The synthesis of peptides used in this example and determination of anti-HIV effect were carried out as described in Example 1. The results of these experiments are shown in FIG. 2. The two peptides, #11 (viz. 111–145P$_6$-C) and #12 (111–148), are modified fragments with altered and/or additional amino acids that are not present in the native subunit. The peptide #12 containing the incorrect amino acid sequence of beta hCG-CT bad no significant effect. The modified CT fragment #11 (111–145$P_6$-C) with seven additional amino acid residues at the C-terminal end displayed a diminished activity with the peak corresponding to the higher end of dose range. None of the tested peptides were toxic to MT-4 cells at the concentration range used in these experiments.

DETAILED DESCRIPTION OF THE DRAWINGS.

FIG. 1. Survival of MT-4 lymphocytes incubated with synthetic beta hCG peptides (#1–#6) following 5–7 days exposure to life strain of HIV-1. The viability data of surviving cells (left Y axis) was obtained using XTT assay and bars represent the means in % values as calculated in relation to viability parameters of mock-infected and untreated controls dead from exposure to HIV. The % values on the left axis were positioned in a fashion that allows estimation of the effect of the test peptides as a function of concentration plotted on the horizontal axis. The experiments were repeated three times and the means of data points are shown.

FIG. 2. Effect of peptides from C-terminal portion of beta hCG on HIV-caused cell death as shown in graphs labeled accordingly. The most potent effect is observed with the peptide #9 which exhibits a typical bell-shaped dose response. The % viability of MT-4 cells corresponding to each dilution of the peptide is shown as a bar which represents the mean from three experiments. The experiments were repeated at least three times and the mean of data points are shown. The % values on the right axis were positioned in a fashion that allows estimation of the effect of the test peptides as a function of ten-fold dilutions of said peptides plotted on the horizontal axis.

Figure 3:
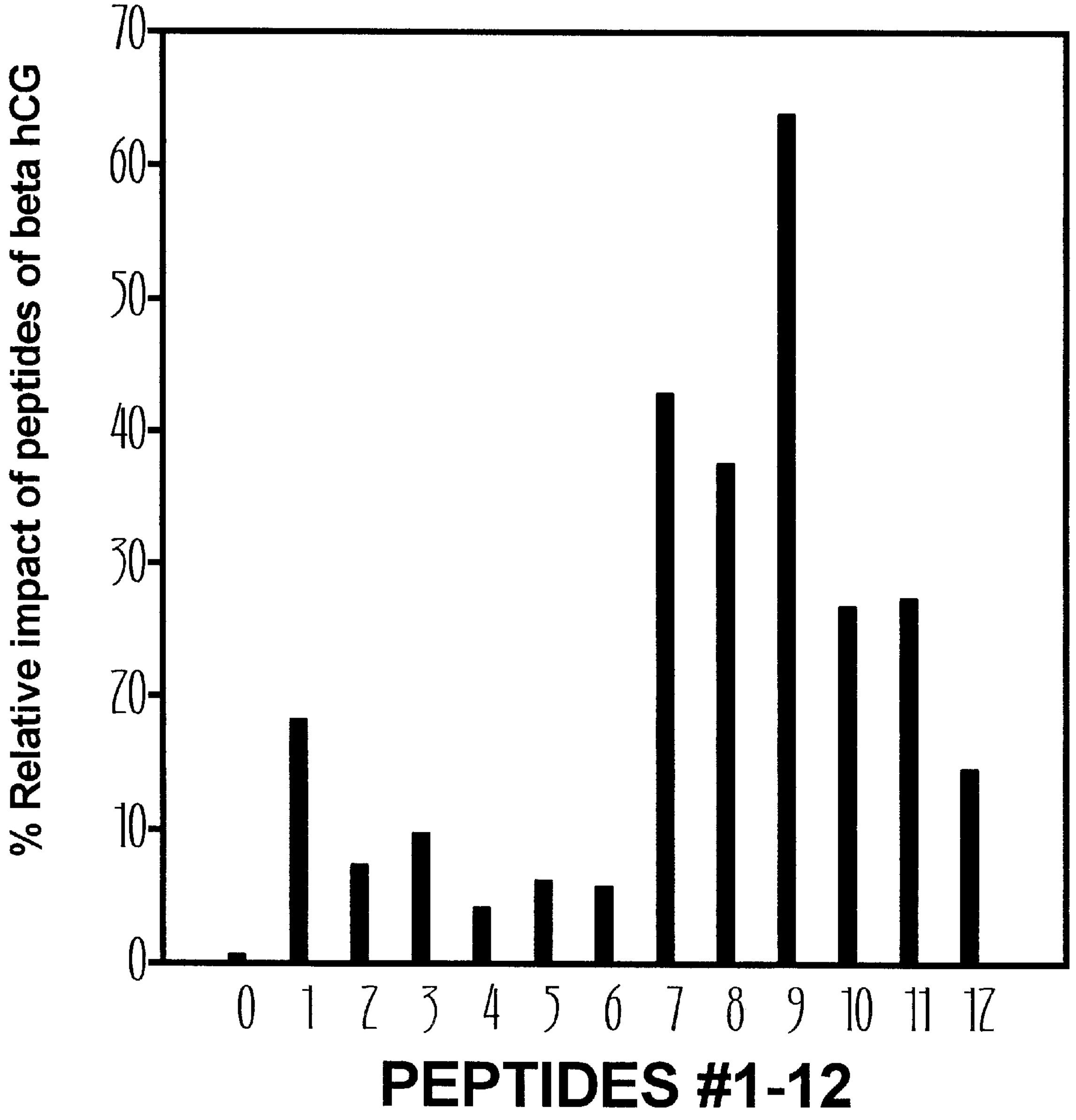
FIG. 3 shows relative impact of peptide fragments of beta hCG defining the anti-HIV activity.

FIG. 3. This figure summarizes the relative impact of 12 tested peptides on the survival of MT-4. Each bar in this figure represents the mean value of all six dilutions of an individual peptide. Although N-terminal portion of beta hCG appears to be relatively more active than the core region this figure reveals a clear trend in the favor of selective activity of CT portion of beta hCG. Histogram shows the relative impact of 12 tested beta hCG peptides on survival of MT4 lymphocytes. Each bar is derived from data displayed in FIGS. 1 & 2 and represents the average effect on viability generated by all six dilutions (100 mcg–1 ng) of an individual peptide. The effect of each peptide is shown relative to a total sum of 100%. Note that the tallest bar corresponds to the peptide #9 spanning across the entire CT region of beta hCG. However, it is can be seen clearly that other peptides from C-terminal region as well as a peptide from N-terminal portion can also display a strong antiviral effect.

The overlapping synthetic peptides comprising three principal domains of beta hCG were tested for their activity against HIV-caused cytopathic effect with the goal of identifying the active site(s) responsible for the antiviral activity. The N-terminal core, C-terminal portions of beta hCG are defined as each being approximately 50 amino acid residues long. The experimental data, representing the survival rate of HIV-exposed MT4 lymphocytes treated with hCG fragments, was obtained for 12 peptides, which together represent almost an entire beta subunit. Although the N-terminal end of hCG contributes to over-all activity, the core region appears to be biologically inert. The obtained results also suggest that the COOH-terminal portion plays the important role in determining the anti-HIV activity (FIG. 3). The peptides #7, #8, and #10, which represent three separate short fragments of the CTP, were of restricted effect. The large-size peptide #12 (111–148) containing the incorrect amino acid sequence of hCG-CTP had no activity. The modified CTP fragment #11(111–145$P_6$-C) with proline and cysteine spacer residues shoved modest activity with the peak corresponding to 1–10 mcg/ml doses. However, a single peptide containing 40 amino acids of the COOH-terminus seemed to be the most potent. This peptide exhibited a pattern of dose response that was identical to the bell-shaped curve observed previously with both native hCG heterodimer and the purified hCG subunit. Interestingly, the effective concentrations of 106–145 peptide were within the same 10 ng–1 mcg dose range as with beta hCG. Although the antiviral assays for testing beta hCG and synthetic peptides of beta hCG were dissimilar, this observation appears to support further the possibility that the anti-HIV activity of hCG is specific to this hormone and is mainly determined by the N-terminal and CT portions of the beta subunit—the shortest fragments of the hormone that retain the anti-HIV activity. This is important, for it reveals the important physiological function of peptides that were previously considered to be lacking in biological activity.

From the standpoint of classical studies, which dealt exclusively with the reproductive function of hCG mediated via hCG/LH receptor, this discovery is extremely surprising. The carboxyl-terminal extension is unique to beta hCG and is not present in any other beta subunit of pituitary hormones including LH. The CTP of beta hCG is specific only to human species and is not present in any other animal species studied so far. It is known that the hCG-CT portion does not bind to hCG/LH receptor and hence is regarded as inert. Furthermore hCG molecule devoid of sugar moiety is considered as not active. The hCG/LH receptor belongs to the 7-transmembrane G-protein linked receptor family. It consists of an extracellular N-terminal half of 341 amino acids capable of high affinity hormone binding, and a membrane-associated C-terminal half of 303 amino acids capable of low affinity hormone binding and receptor activation via cAMP induction. The activity of the carboxy-terminus of beta hCG was merely associated with the extension of plasma half-life by reducing the metabolic clearance and increase in the stability of heterodimer. However, these properties were attributed to the carbohydrate moiety consisting of four serine O-linked oligosaccharides, since synthetic nonglycosylated peptides were reportedly not active. Synthetic peptides used in examples hereabove lack carbohydrates which indicates that the antiviral activity is determined specifically by the amino acid residues of hCG-CT arranged in a specific sequence.

The addition of hCG-CT portion to the core was attributed to the loss of the termination codon of an ancestral beta-like gene and has been regarded as an accidental and neutral event in the evolution of the glycoprotein hormone. This portion is unique to humans but intensive structure/function studies have failed to reveal a definitive role for it.

Human chemoattractant chemokines RANTES and MIP-1alpha/MIP-1beta were recently identified as HIV-suppressive factors. Following this discovery different variants of receptors for these chemokines, e.g., CXCR4 (fusin) and CC-CKR-5 (CCR5), were proposed as fusion co-factors or co-receptors for HIV. Curiously, these cellular ligands belong to the same family of seven-transmembrane G-protein coupled receptors such as hCG/LH receptor—which was recently found on T lymphocytes. Similar to hCG or beta hCG, these chemokines had also exhibited a disparate activity toward T lymphocyte-tropic and macrophage-tropic HIV strains. While it cannot be ruled out that hCG, also known as a potent chemoattractant, may act through the mechanism attributed to RANTES or MIP-1alpha/MIP-1beta, the fact that the beta hCG-CT portion per se does not bind to the receptor may indicate other mechanisms than competitive interaction. In general, it is quite certain that the interaction of chemoattractants with their respective ligands plays an important role in host defence, although the sequence of events leading either to the elimination or the tolerance of an invading pathogen, tumor, or blastocyst is not yet clear. In this respect the anti-tumor and anti-infectious properties of hCG are possibly related to the effect exerted by interferon—another immune hormone that has shared functions with hCG This possibility is not entirely groundless, especially when one considers the fact that type one interferons can replace the luteotrophic function of hCG—the phenomenon that occurs in certain animal species lacking hCG. It is known that the antiviral action of human interferon can be blocked by hCG, suggesting that these hormones share a common binding site on the cell surface or share a similar mechanism of action. However, such an explanation for. the mode of hCG action might be not as simple as it may appear as interferon does not share any structure homology with hCG and interferon receptor is not related to hCG/LH receptor.

The discovery of the antiviral activity of hCG has great potential in the prevention and treatment of AIDS. While hCG itself can be used in AIDS therapy, due to concerns in regard to hormonal side-effects, especially in women, it is preferable that beta subunit is used. However, synthetic peptides seem to be more suitable for this purpose since they can be produced with higher quality control than the purification of beta hCG subunit from the urine of pregnant women. These peptides can be prepared by chemical synthesis methodology or produced by recombinant DNA technology according to the methods readily known to those of ordinary skill in the art. Ultimately, the understanding of the antiviral activity of hCG will lead to the discovery of therapeutically useful compounds derived from the rational design of peptide mimetics with higher stability and the potential convenience of being orally available. The design of peptide mimetics of hCG can be achieved by the methods which are readily known to those of ordinary skill in the art.

In conclusion, it has been discovered by this inventor that select peptide fragments from the beta subunit of hCG are responsible for anti-HIV activity. The results presented in the 3 figures demonstrate that N-terminal and C-terminal portions of beta hCG are effective against HIV infection in vitro at doses which are not toxic. The pharmaceutical formulation containing peptide fragments of beta hCG as active ingredients may be suitably administered together with a pharmaceutically acceptable carrier known in the art. The exact form of delivery will depend on the particular need, being either systemic treatment of HIV infection or prevention of transmission and spread of HIV by using topical or systemic formulation.

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:

1. A method of treating HIV infection in human cells and tissues or inhibiting the spread of human immunodeficiency virus (HIV) to uninfected human cells and tissues comprising administering to a human host an anti-HIV effective amount of a peptide fragment of amino acids 1–50 or 100–145 of SEQ ID NO:1 of beta human chorionic gonadotropin (hCG) or an anti-HIV fragment thereof containing at least four contiguous amino acid units of said amino acids 1–50 or 100–145 for a time and under conditions effective to reduce HIV infection or spread of HIV to uninfected human cells.

2. The method according to claim 1 wherein said peptide fragment contains at least 10 amino acid units.

3. The method according to claim 1 wherein said peptide fragment is Sequence I.D. No. 13 or an anti-HIV fragment thereof.

4. The method according to claim 1 wherein said peptide fragment is Sequence I.D. No. 10 or an anti-HIV fragment thereof containing at least 5 amino acids.

5. A method of treating an HIV infection in a patient comprising administering to said patient an anti-HIV effective amount of a peptide fragment corresponding to amino acids 1–50, or 100–145 of beta hCG, or an anti-HIV fragment thereof containing at least five amino acid units for a time and under conditions effective to reduce HIV infection.

6. The method according to claim 5 wherein said peptide fragment is Sequence I.D. No. 10 or an anti-HIV fragment thereof containing at least 5 amino acids.

7. The method according to claim 5 wherein said peptide fragment contains at least 10 amino acid units.

8. The method according to claim 5 wherein said peptide fragment contains at least 40 amino acid units.

9. The method according to claim 5 wherein said peptide fragment reaches a level of about 1 ng to about 500 mcg/ml in said patient's body fluids.

10. The method according to claim 9 wherein said body fluids are selected from the group consisting of blood, plasma and serum.

11. The method according to claim 5 wherein said peptide fragment is administered in combination with at least one agent selected from the group consisting of warfarin, coumarins, bestatin, levamisole, estrogen, progesterone, dexamethasone, indomethacin, acetaminophen, cimetidine, and gramicidin.

12. A method of treating the symptoms of acquired immunodeficiency syndrome (AIDS) in a patient comprising administering to a human host an anti-HIV effective amount of a peptide fragment of amino acids 1–50 or 100–145 of SEQ ID NO:1 of beta human chorionic gonadotropin (hCG) or an anti-HIV fragment thereof containing at least four contiguous amino acid units of said amino acids 1–50 or 100–145 for a time and under conditions effective to reduce HIV infection in said patient.

13. The method according to claim 12 wherein said peptide fragment is Sequence I.D. No. 10 or an anti-HIV fragment thereof containing at least 5 amino acids.

14. The method according to claim 12 wherein said peptide fragment contains at least 10 amino acid units.

15. The method according to claim 12 wherein said peptide fragment contains at least 40 amino acid units.

16. The method according to claim 12 wherein said peptide fragment reaches levels of about 1 ng to about 500 mcg/ml in said patient's body fluids.

17. A method of inhibiting the spread of human immunodeficiency virus (HIV) infection in a fetus of an HIV infected mother comprising administering to said mother of said fetus anti-HIV effective amount of a peptide fragment of amino acids 1–50 or 100–145 of SEQ ID NO:1 of beta human chorionic gonadotropin (hCG) or an anti-HIV fragment thereof containing at least four contiguous amino acid units of said amino acids 1–50 or 100–145 for a time and under conditions effective to inhibit the spread of human immunodeficiency virus (HIV) infection in said fetus.

18. The method according to claim 17 wherein said peptide fragment is Sequence I.D. No. 10 or an anti-HIV fragment thereof containing at least 5 amino acids.

* * * * *

```
                        SEQUENCE LISTING


(1) GENERAL INFORMATION:

   (iii) NUMBER OF SEQUENCES:  13


(2) INFORMATION FOR SEQ ID NO: 1:

     (i) SEQUENCE CHARACTERISTICS:
          (A) LENGTH:  145 Amino Acid Units
          (B) TYPE:  Amino Acid
          (C) STRANDEDNESS:  Single Stranded
          (D) TOPOLOGY:  Linear

    (ii) MOLECULE TYPE: Protein Subunit
          (A) DESCRIPTION: Amino Acid Corresponding to Beta Subunit
               of Human Chorionic Gonadotropin

   (iii) HYPOTHETICAL:  No

    (iv) ANTI-SENSE:  No

    (vi) ORIGINAL SOURCE: Sequence

   (vii) IMMEDIATE SOURCE: N/A

  (viii) POSITION IN GENOME: N/A

    (ix) FEATURE:
          (A) NAME/KEY:  145 Units of Beta Subunit of Human Chorionic
               Gonadotropin
          (B) LOCATION:  N/A
          (C) IDENTIFICATION METHOD:  Sequencing

     (x) PUBLICATION INFORMATION:
          (A) AUTHORS: CARLSEN, Robert B.,
```

-continued

```
              BAHL, Ohm P.
              SWAMINATHAN, N.
         (B) TITLE:  HUMAN CHORIONIC GONADOTROPIN
         (C) JOURNAL: THE JOURNAL OF BIOLOGICAL CHEMISTRY
         (D) VOLUME:  248
         (F) PAGES:  6810-6825
         (G) DATE:   1973

    (xi) SEQUENCE DESCRIPTION: SEQ ID NO: 1:

Ser Lys Glu Pro Leu Arg Pro Arg Cys Arg Pro Ile Asn Ala Thr
                5                   10                  15

Leu Ala Val Glu Lys Glu Gly Cys Pro Val Cys Ile Thr Val Asn
                20                  25                  30

Thr Thr Ile Cys Ala Gly Tyr Cys Pro Thr Met Thr Arg Val Leu
                35                  40                  45

Gln Gly Val Leu Pro Ala Leu Pro Gln Val Val Cys Asn Tyr Arg
                50                  55                  60

Asp Val Arg Phe Glu Ser Ile Arg Leu Pro Gly Cys Pro Arg Gly
                65                  70                  75

Val Asn Pro Val Val Ser Tyr Ala Val Ala Leu Ser Cys Gln Cys
                80                  85                  90

Ala Leu Cys Arg Arg Ser Thr Thr Asp Cys Gly Gly Pro Lys Asp
                95                  100                 105

His Pro Leu Thr Cys Asp Asp Pro Arg Phe Gln Asp Ser Ser Ser
                110                 115                 120

Ser Lys Ala Pro Pro Pro Ser Leu Pro Ser Pro Ser Arg Leu Pro
                125                 130                 135

Gly Pro Ser Asp Thr Pro Ile Leu Pro Gln
                140                 145


(2) INFORMATION FOR SEQ ID NO: 2:

     (i) SEQUENCE CHARACTERISTICS:
         (A) LENGTH: 13 amino acid units
         (B) TYPE:  Amino Acid
         (C) STRANDEDNESS:  Single Stranded
         (D) TOPOLOGY: Not Relevant

    (ii) MOLECULE TYPE: Protein Subunit
         (A) DESCRIPTION: 13 amino acids corresponding to amino
              acids 20-32 of the beta subunit of human chorionic
              gonadotropin

   (iii) HYPOTHETICAL:  No

    (iv) ANTI-SENSE:  No

    (vi) ORIGINAL SOURCE: Chemical Synthesis

   (vii) IMMEDIATE SOURCE:N/A

  (viii) POSITION IN GENOME: N/A

    (ix) FEATURE:
         (A) NAME/KEY:  Oligopeptide corresponding to Amino Acids 20-32
              of Beta Subunit of Human Chorionic Gonatropin
         (B) LOCATION:  Beta subunit of Human Chorionic Gonadotropin
         (C) IDENTIFICATION METHOD:  Chemical synthesis

     (x) PUBLICATION INFORMATION:
         (A) AUTHORS: STEVENS, Vernon C.
         (B) TITLE:  ANTIGENIC MODIFICATION OF AMINO ACIDS
         (C) JOURNAL: UNITED STATES PATENT NUMBER 4,302,386
         (D) VOLUME:  N/A
         (F) PAGES:  N/A
         (G) DATE:   November 24, 1981

    (xi) SEQUENCE DESCRIPTION: SEQ ID NO: 2:
```

-continued

```
Lys Glu Gly Cys Pro Val Cys Ile Thr Val Asn Thr Thr
                5                   10


(2) INFORMATION FOR SEQ ID NO: 3:

     (i) SEQUENCE CHARACTERISTICS:
          (A) LENGTH: 13 amino acid units
          (B) TYPE:  Amino Acid
          (C) STRANDEDNESS:  Single Stranded
          (D) TOPOLOGY: Not Relevant

    (ii) MOLECULE TYPE: Protein Subunit
          (A) DESCRIPTION: 13 amino acids corresponding to amino
               acids 30-42 of the beta subunit of human chorionic
               gonadotropin

   (iii) HYPOTHETICAL:  No

    (iv) ANTI-SENSE:  No

    (vi) ORIGINAL SOURCE: Chemical Synthesis

   (vii) IMMEDIATE SOURCE:N/A

  (viii) POSITION IN GENOME: N/A

    (ix) FEATURE:
          (A) NAME/KEY:  Oligopeptide corresponding to Amino Acids 30-42
               of Beta Subunit of Human Chorionic Gonatropin
          (B) LOCATION:  Beta subunit of Human Chorionic Gonadotropin
          (C) IDENTIFICATION METHOD:  Chemical synthesis

     (x) PUBLICATION INFORMATION:
          (A) AUTHORS: STEVENS, Vernon C.
          (B) TITLE:  ANTIGENIC MODIFICATION of Amino Acid
          (C) JOURNAL: UNITED STATES PATENT NUMBER 4,302,386
          (D) VOLUME:  N/A
          (F) PAGES:  N/A
          (G) DATE:   November 24, 1981

    (xi) SEQUENCE DESCRIPTION: SEQ ID NO: 3:

Asn Thr Thr Ile Cys Ala Gly Tyr Cys Pro Thr Met Thr
                5                   10


(2) INFORMATION FOR SEQ ID NO: 4:

     (i) SEQUENCE CHARACTERISTICS:
          (A) LENGTH: 13 amino acid units
          (B) TYPE:  Amino Acid
          (C) STRANDEDNESS:  Single Stranded
          (D) TOPOLOGY: Not Relevant

    (ii) MOLECULE TYPE: Protein Subunit
          (A) DESCRIPTION: 13 amino acids corresponding to amino
               acids 50-62 of the beta subunit of human chorionic
               gonadotropin

   (iii) HYPOTHETICAL:  No

    (iv) ANTI-SENSE:  No

    (vi) ORIGINAL SOURCE: Chemical Synthesis

   (vii) IMMEDIATE SOURCE:N/A

  (viii) POSITION IN GENOME: N/A

    (ix) FEATURE:
          (A) NAME/KEY:  Oligopeptide corresponding to Amino Acids 50-62
               of Beta Subunit of Human Chorionic Gonatropin
          (B) LOCATION:  Beta subunit of Human Chorionic Gonadotropin
          (C) IDENTIFICATION METHOD:  Chemical synthesis

     (x) PUBLICATION INFORMATION:
          (A) AUTHORS: STEVENS, Vernon C.
```

-continued (B) TITLE: ANTIGENIC MODIFICATION OF AMINO ACIDS
(C) JOURNAL: UNITED STATES PATENT NUMBER 4,302,386
(D) VOLUME: N/A
(F) PAGES: N/A
(G) DATE: November 24, 1981

(xi) SEQUENCE DESCRIPTION: SEQ ID NO: 4:

```
Pro Ala Leu Pro Gln Val Val Cys Asn Tyr Arg Asp Val
                5                   10
```

(2) INFORMATION FOR SEQ ID NO: 5:

(i) SEQUENCE CHARACTERISTICS:
(A) LENGTH: 13 amino acid units
(B) TYPE: Amino Acid
(C) STRANDEDNESS: Single Stranded
(D) TOPOLOGY: Not Relevant (ii) MOLECULE TYPE: Protein Subunit
(A) DESCRIPTION: 13 amino acids corresponding to amino acids 60-72 of the beta subunit of human chorionic gonadotropin (iii) HYPOTHETICAL: No (iv) ANTI-SENSE: No (vi) ORIGINAL SOURCE: Chemical Synthesis (vii) IMMEDIATE SOURCE:N/A (viii) POSITION IN GENOME: N/A (ix) FEATURE:
(A) NAME/KEY: Oligopeptide corresponding to Amino Acids 60-72 of Beta Subunit of Human Chorionic Gonatropin
(B) LOCATION: Beta subunit of Human Chorionic Gonadotropin
(C) IDENTIFICATION METHOD: Chemical synthesis (x) PUBLICATION INFORMATION:
(A) AUTHORS: STEVENS, Vernon C.
(B) TITLE: ANTIGENIC MODIFICATION OF AMINO ACIDS
(C) JOURNAL: UNITED STATES PATENT NUMBER 4,302,386
(D) VOLUME: N/A
(F) PAGES: N/A
(G) DATE: November 24, 1981

(xi) SEQUENCE DESCRIPTION: SEQ ID NO: 5:

```
Arg Asp Val Arg Phe Glu Ser Ile Arg Leu Pro Gly Cys
                5                   10
```

(2) INFORMATION FOR SEQ ID NO: 6:

(i) SEQUENCE CHARACTERISTICS:
(A) LENGTH: 13 amino acid units
(B) TYPE: Amino Acid
(C) STRANDEDNESS: Single Stranded
(D) TOPOLOGY: Not Relevant (ii) MOLECULE TYPE: Protein Subunit
(A) DESCRIPTION: 13 amino acids corresponding to amino acids 80-92 of the beta subunit of human chorionic gonadotropin (iii) HYPOTHETICAL: No (iv) ANTI-SENSE: No (vi) ORIGINAL SOURCE: Chemical Synthesis (vii) IMMEDIATE SOURCE:N/A (viii) POSITION IN GENOME: N/A (ix) FEATURE:

-continued (A) NAME/KEY: Oligopeptide corresponding to Amino Acids 80-92 of Beta Subunit of Human Chorionic Gonatropin
(B) LOCATION: Beta subunit of Human Chorionic Gonadotropin
(C) IDENTIFICATION METHOD: Chemical synthesis (x) PUBLICATION INFORMATION:
(A) AUTHORS: STEVENS, Vernon C.
(B) TITLE: ANTIGENIC MODIFICATION OF AMINO ACIDS
(C) JOURNAL: UNITED STATES PATENT NUMBER 4,302,386
(D) VOLUME: N/A
(F) PAGES: N/A
(G) DATE: November 24, 1981

(xi) SEQUENCE DESCRIPTION: SEQ ID NO: 6:

```
Val Ser Tyr Ala Val Ala Leu Ser Cys Gln Cys Ala Leu
                5                   10
```

(2) INFORMATION FOR SEQ ID NO: 7:

(i) SEQUENCE CHARACTERISTICS:
(A) LENGTH: 13 amino acid units
(B) TYPE: Amino Acid
(C) STRANDEDNESS: Single Stranded
(D) TOPOLOGY: Not Relevant (ii) MOLECULE TYPE: Protein Subunit
(A) DESCRIPTION: 13 amino acids corresponding to amino acids 90-102 of the beta subunit of human chorionic gonadotropin (iii) HYPOTHETICAL: No (iv) ANTI-SENSE: No (vi) ORIGINAL SOURCE: Chemical Synthesis (vii) IMMEDIATE SOURCE:N/A (viii) POSITION IN GENOME: N/A (ix) FEATURE:
(A) NAME/KEY: Oligopeptide corresponding to Amino Acids 90-102 of Beta Subunit of Human Chorionic Gonatropin
(B) LOCATION: Beta subunit of Human Chorionic Gonadotropin
(C) IDENTIFICATION METHOD: Chemical synthesis (x) PUBLICATION INFORMATION:
(A) AUTHORS: STEVENS, Vernon C.
(B) TITLE: ANTIGENIC MODIFICATION OF AMINO ACIDS
(C) JOURNAL: UNITED STATES PATENT NUMBER 4,302,386
(D) VOLUME: N/A
(F) PAGES: N/A
(G) DATE: November 24, 1981

(xi) SEQUENCE DESCRIPTION: SEQ ID NO: 7:

```
Cys Ala Leu Cys Arg Arg Ser Thr Thr Asp Cys Gly Gly
                5                   10
```

(2) INFORMATION FOR SEQ ID NO: 8:

(i) SEQUENCE CHARACTERISTICS:
(A) LENGTH: 13 amino acid units
(B) TYPE: Amino Acid
(C) STRANDEDNESS: Single Stranded
(D) TOPOLOGY: Not Relevant (ii) MOLECULE TYPE: Protein Subunit
(A) DESCRIPTION: 13 amino acids corresponding to amino acids 100-112 of the beta subunit of human chorionic gonadotropin (iii) HYPOTHETICAL: No (iv) ANTI-SENSE: No -continued (vi) ORIGINAL SOURCE: Chemical Synthesis (vii) IMMEDIATE SOURCE:N/A (viii) POSITION IN GENOME: N/A (ix) FEATURE:
(A) NAME/KEY: Oligopeptide corresponding to Amino Acids 100-112 of Beta Subunit of Human Chorionic Gonatropin
(B) LOCATION: Beta subunit of Human Chorionic Gonadotropin
(C) IDENTIFICATION METHOD: Chemical synthesis (x) PUBLICATION INFORMATION:
(A) AUTHORS: STEVENS, Vernon C.
(B) TITLE: ANTIGENIC MODIFICATION OF AMINO ACIDS
(C) JOURNAL: UNITED STATES PATENT NUMBER 4,302,386
(D) VOLUME: N/A
(F) PAGES: N/A
(G) DATE: November 24, 1981

(xi) SEQUENCE DESCRIPTION: SEQ ID NO: 8:

```
Cys Gly Gly Pro Lys Asp His Pro Leu Thr Cys Asp Asp
                5                       10
```

(2) INFORMATION FOR SEQ ID NO: 9:

(i) SEQUENCE CHARACTERISTICS:
(A) LENGTH: 13 amino acid units
(B) TYPE: Amino Acid
(C) STRANDEDNESS: Single Stranded
(D) TOPOLOGY: Not Relevant (ii) MOLECULE TYPE: Protein Subunit
(A) DESCRIPTION: 13 amino acids corresponding to amino acids 120-132 of the beta subunit of human chorionic gonadotropin (iii) HYPOTHETICAL: No (iv) ANTI-SENSE: No (vi) ORIGINAL SOURCE: Chemical Synthesis (vii) IMMEDIATE SOURCE:N/A (viii) POSITION IN GENOME: N/A (ix) FEATURE:
(A) NAME/KEY: Oligopeptide corresponding to Amino Acids 120-132 of Beta Subunit of Human Chorionic Gonatropin
(B) LOCATION: Beta subunit of Human Chorionic Gonadotropin
(C) IDENTIFICATION METHOD: Chemical synthesis (x) PUBLICATION INFORMATION:
(A) AUTHORS: STEVENS, Vernon C.
(B) TITLE: ANTIGENIC MODIFICATION OF AMINO ACIDS
(C) JOURNAL: UNITED STATES PATENT NUMBER 4,302,386
(D) VOLUME: N/A
(F) PAGES: N/A
(G) DATE: November 24, 1981

(xi) SEQUENCE DESCRIPTION: SEQ ID NO: 9:

```
Ser Ser Lys Ala Pro Pro Pro Ser Leu Pro Ser Pro Ser
                5                   10
```

(2) INFORMATION FOR SEQ ID NO: 10:

(i) SEQUENCE CHARACTERISTICS:
(A) LENGTH: 40 amino acid units
(B) TYPE: Amino Acid
(C) STRANDEDNESS: Single Stranded
(D) TOPOLOGY: Not Relevant (ii) MOLECULE TYPE: Protein Subunit
(A) DESCRIPTION: 40 amino acids corresponding to amino -continued acids 106-145 of the beta subunit of human chorionic gonadotropin (iii) HYPOTHETICAL: No (iv) ANTI-SENSE: No (vi) ORIGINAL SOURCE: Chemical Synthesis (vii) IMMEDIATE SOURCE:N/A (viii) POSITION IN GENOME: N/A (ix) FEATURE:
(A) NAME/KEY: Oligopeptide corresponding to Amino Acids 106-145 of Beta Subunit of Human Chorionic Gonatropin
(B) LOCATION: Beta subunit of Human Chorionic Gonadotropin
(C) IDENTIFICATION METHOD: Chemical synthesis (x) PUBLICATION INFORMATION:
(A) AUTHORS: STEVENS, Vernon C.
(B) TITLE: ANTIGENIC MODIFICATION OF AMINO ACIDS
(C) JOURNAL: UNITED STATES PATENT NUMBER 4,302,386
(D) VOLUME: N/A
(F) PAGES: N/A
(G) DATE: November 24, 1981

(xi) SEQUENCE DESCRIPTION: SEQ ID NO: 10:

```
His Pro Leu Thr Cys Asp Asp Pro Arg Phe Gln Asp Ser Ser Ser
                5                   10                  15

Ser Lys Ala Pro Pro Pro Ser Leu Pro Ser Pro Ser Arg Leu Pro
                20                  25                  30

Gly Pro Ser Asp Thr Pro Ile Leu Pro Gln
                35                  40
```

(2) INFORMATION FOR SEQ ID NO: 11:

(i) SEQUENCE CHARACTERISTICS:
(A) LENGTH: 16 amino acid units
(B) TYPE: Amino Acid
(C) STRANDEDNESS: Single Stranded
(D) TOPOLOGY: Not Relevant (ii) MOLECULE TYPE: Protein Subunit
(A) DESCRIPTION: 16 amino acids corresponding to amino acids 130-145 of the beta subunit of human chorionic gonadotropin (iii) HYPOTHETICAL: No (iv) ANTI-SENSE: No (vi) ORIGINAL SOURCE: Chemical Synthesis (vii) IMMEDIATE SOURCE:N/A (viii) POSITION IN GENOME: N/A (ix) FEATURE:
(A) NAME/KEY: Oligopeptide corresponding to Amino Acids 130-145 of Beta Subunit of Human Chorionic Gonatropin
(B) LOCATION: Beta subunit of Human Chorionic Gonadotropin
(C) IDENTIFICATION METHOD: Chemical synthesis (x) PUBLICATION INFORMATION:
(A) AUTHORS: STEVENS, Vernon C.
(B) TITLE: ANTIGENIC MODIFICATION OF AMINO ACIDS
(C) JOURNAL: UNITED STATES PATENT NUMBER 4,302,386
(D) VOLUME: N/A
(F) PAGES: N/A
(G) DATE: November 24, 1981

(xi) SEQUENCE DESCRIPTION: SEQ ID NO: 11:

```
Ser Pro Ser Arg Leu Pro Gly Pro Ser Asp Thr Pro Ile Leu Pro Gln
```

-continued 5 10 15

(2) INFORMATION FOR SEQ ID NO: 12:

(i) SEQUENCE CHARACTERISTICS:
(A) LENGTH: 43 amino acid units
(B) TYPE: Amino Acid
(C) STRANDEDNESS: Single Stranded
(D) TOPOLOGY: Not Relevant (ii) MOLECULE TYPE: Protein Subunit
(A) DESCRIPTION: 43 amino acids corresponding to amino acids 111-145 of the beta subunit of human chorionic gonadotropin plus a spacer consisting of 6 proline amino acid units and 1 cysteine residue at C-terminal end (iii) HYPOTHETICAL: No (iv) ANTI-SENSE: No (vi) ORIGINAL SOURCE: Chemical Synthesis (vii) IMMEDIATE SOURCE:N/A (viii) POSITION IN GENOME: N/A (ix) FEATURE:
(A) NAME/KEY: Oligopeptide corresponding to Amino Acids 111-145 of Beta Subunit of Human Chorionic Gonatropin Plus Seven Amino Acid Spacer
(B) LOCATION: Beta subunit of Human Chorionic Gonadotropin Plus Spacer
(C) IDENTIFICATION METHOD: Chemical synthesis (x) PUBLICATION INFORMATION:
(A) AUTHORS: STEVENS, Vernon C.
(B) TITLE: ANTIGENIC MODIFICATION OF AMINO ACIDS
(C) JOURNAL: UNITED STATES PATENT NUMBER 4,302,386
(D) VOLUME: N/A
(F) PAGES: N/A
(G) DATE: November 24, 1981

(xi) SEQUENCE DESCRIPTION: SEQ ID NO: 12:

```
Asp Asp Pro Arg Phe Gln Asp Ser Ser Ser Ser Lys Ala Pro Pro
                5                   10                  15

Pro Ser Leu Pro Ser Pro Ser Arg Leu Pro Gly Pro Ser Asp Asp
                20                  25                  30

Thr Pro Ile Leu Pro Gln Pro Pro Pro Pro Pro Pro Cys
                35                  40
```

(2) INFORMATION FOR SEQ ID NO: 13:

(i) SEQUENCE CHARACTERISTICS:
(A) LENGTH: 45 amino acid units
(B) TYPE: Amino Acid
(C) STRANDEDNESS: Single Stranded
(D) TOPOLOGY: Not Relevant (ii) MOLECULE TYPE: Protein Subunit
(A) DESCRIPTION: 45 amino acids corresponding to amino acids 1-45 of the beta subunit of human chorionic gonadotropin (iii) HYPOTHETICAL: No (iv) ANTI-SENSE: No (vi) ORIGINAL SOURCE: Chemical Synthesis (vii) IMMEDIATE SOURCE:N/A (viii) POSITION IN GENOME: N/A -continued

```
(ix) FEATURE:
      (A) NAME/KEY:  Oligopeptide corresponding to Amino Acids 1-45
           of Beta Subunit of Human Chorionic Gonatropin
      (B) LOCATION:  Beta subunit of Human Chorionic Gonadotropin
           Plus Spacer
      (C) IDENTIFICATION METHOD:  Chemical synthesis

 (x) PUBLICATION INFORMATION:
      (A) AUTHORS: STEVENS, Vernon C.
      (B) TITLE:  ANTIGENIC MODIFICATION OF AMINO ACIDS
      (C) JOURNAL: UNITED STATES PATENT NUMBER 4,302,386
      (D) VOLUME:  N/A
      (F) PAGES:  N/A
      (G) DATE:   November 24, 1981

(xi) SEQUENCE DESCRIPTION: SEQ ID NO: 13:

Ser Lys Glu Pro Leu Arg Pro Arg Cys Arg Pro Ile Asn Ala Thr
                5                   10                  15

Leu Ala Val Glu Lys Glu Gly Cys Pro Val Cys Ile Thr Val Asn
                20                  25                  30

Thr Thr Ile Cys Ala Gly Tyr Cys Pro Thr Met Thr Arg Val Leu
                35                  40                  45
```